United States Patent
Li et al.

(10) Patent No.: US 10,987,396 B2
(45) Date of Patent: *Apr. 27, 2021

(54) COMPOSITION FOR IMPROVING INTERNAL CIRCULATION AND DELAYING AGING AND APPLICATION THEREOF

(71) Applicant: GUIZHOU JIN QIAN FRUIT BIOTECHNOLOGY CO., LTD., Guizhou (CN)

(72) Inventors: Shouqian Li, Bijie (CN); Shouyue Li, Bijie (CN); Yu Zhou, Bijie (CN)

(73) Assignee: GUIZHOU JIN QIAN FRUIT BIOTECHNOLOGY CO., LTD., Guizhou (CN)

(*) Notice: Subject to any disclaimer, the term of this patent is extended or adjusted under 35 U.S.C. 154(b) by 62 days.

This patent is subject to a terminal disclaimer.

(21) Appl. No.: 16/603,780

(22) PCT Filed: Apr. 8, 2018

(86) PCT No.: PCT/CN2018/082125
§ 371 (c)(1),
(2) Date: Oct. 8, 2019

(87) PCT Pub. No.: WO2018/188525
PCT Pub. Date: Oct. 18, 2018

(65) Prior Publication Data
US 2021/0069278 A1    Mar. 11, 2021

(30) Foreign Application Priority Data
Apr. 9, 2017 (CN) .......................... 201710226412.0

(51) Int. Cl.
| A61K 36/00 | (2006.01) |
| A61K 36/738 | (2006.01) |
| A61K 36/185 | (2006.01) |
| A61K 35/644 | (2015.01) |
| A61K 36/52 | (2006.01) |
| A61K 36/752 | (2006.01) |
| A61P 39/06 | (2006.01) |
| A23L 33/105 | (2016.01) |
| A23L 25/00 | (2016.01) |
| A23L 21/25 | (2016.01) |
| A61K 9/00 | (2006.01) |

(52) U.S. Cl.
CPC ............ *A61K 36/738* (2013.01); *A23L 21/25* (2016.08); *A23L 25/00* (2016.08); *A23L 33/105* (2016.08); *A61K 9/0095* (2013.01); *A61K 35/644* (2013.01); *A61K 36/185* (2013.01); *A61K 36/52* (2013.01); *A61K 36/752* (2013.01); *A61P 39/06* (2018.01); *A23V 2002/00* (2013.01); *A61K 2236/33* (2013.01)

(58) Field of Classification Search
CPC ...................................... A61K 36/00
USPC ........................................... 424/725
See application file for complete search history.

(56) References Cited

FOREIGN PATENT DOCUMENTS

| CN | 1491585 A | 4/2004 |
| CN | 101449790 A | 6/2009 |
| CN | 202618209 U | 12/2012 |

OTHER PUBLICATIONS

Huang, Rugiang et al,. "Preparation of Health-Care Tablet with Phyllanthus and Lemon", Modern Food Science and Technology, vol. 25, No. 2, Feb. 15, 2009 (Feb. 15, 2009) pp. 195-197 (with English Abstract).

Liu, Chunmei et al., "Research and Development of Rosa Roxburghii Tratt Vinegar Beverage", China Brewing, No. 10, Dec. 31, 2009 (Dec. 31, 2009) pp. 155-157 (with English Abstract).

International Search Report (in English and Chinese) issued in PCT/CN2018/082125, dated Jul. 11, 2018; ISA/CN.

*Primary Examiner* — Michael V Meller
(74) *Attorney, Agent, or Firm* — Harness, Dickey & Pierce, P.L.C.

(57) ABSTRACT

The present invention discloses a composition for improving internal circulation and delaying aging and application thereof, and the composition is prepared by *Rosa roxburghii*, *Phyllanthus emblica*, honey, walnut and *Citrus limon* as raw materials.

3 Claims, No Drawings

COMPOSITION FOR IMPROVING INTERNAL CIRCULATION AND DELAYING AGING AND APPLICATION THEREOF

CROSS REFERENCE TO RELATED APPLICATIONS

This application is a U.S. National Phase Application under 35 U.S.C. 371 of International Application No. PCT/CN2018/082125 filed on Apr. 8, 2018, which claims the benefit of priority from Chinese Patent Application No. 201710226412.0 filed Apr. 9, 2017. The entire disclosures of all of the above applications are incorporated herein by reference.

TECHNICAL FIELD

The present invention belongs to the technical field of pharmaceuticals, and specifically relates to a composition for improving internal circulation and delaying aging and an application thereof, and the composition has significant therapeutic effect in the regulation of Qi functions of visceral organs, expelling of vivotoxins and improvement of internal circulation, and has the efficacy of improving body functions and delaying aging.

BACKGROUND

Aging refers to a progressive process that progressive hypofunction and decline of reserve capacity occur in functional activities of organs in human body with age after mature. It is mainly featured by lassitude, waist-leg weakness, amnesia, poor appetite and insomnia, short breath and tiredness, hair loss and loose tooth, intolerance of cold and cold limbs.

At present, there are different opinions on the occurrence mechanism of aging, modern medicine studies believe that aging correlates to the change of in-vivo oxyradicals, endocrine abnormality, brain damage, protein denaturation, inheritance and other factors; traditional Chinese medicine researchers and scholars believe that aging is mainly caused by kidney deficiency, deficiency of spleen and stomach, stagnation of Qi and blood, etc., and mainly manifested by decline of visceral functions, aging appearance and functional degeneration, functional decline of organs, tissues, limbs and bones, etc. In recent years, studies on the theory of aging caused by stagnation of Qi and blood based upon traditional Chinese medicine have been increasingly concerned by traditional Chinese medicine researchers and scholars at home and abroad, showing a theory of dissipative structure, namely: human body is regarded as a dissipative structure which is a system capable of keeping homeostasis in the course of material/energy exchange with the external environment, and when the system is in a stagnation status for a long time, it fails to achieve effect material/energy exchange to supplement the "substance" demanded by daily activities of our human body, thus causing continuous dissipation of nutrient substances, accumulation of hazardous substances, resulting in aging. Researches of modern traditional Chinese medicine show that there is a disturbance of blood circulation and microcirculation in human body with age, which is easy to form blood stasis, causing disturbance of Qi and blood circulation, failure of visceral nourishment and damage of gasification function; meanwhile, metabolites may be not discharged out of body freely and accumulated in body, causing body toxication, thus creating a vicious circle and accelerating aging.

With the gradual improvement of people's life, people's health-care consciousness has enhanced gradually, and moreover, with the social aging in recent years, the market requires 112q1q increasingly high demand for the products capable of regulating internal circulation, improving body functions and delaying aging. Currently, the common anti-aging products are mainly precious Chinese herbal medicines and preparations thereof, such as: *Ginseng* Royal Jelly, *Ginseng* tablets, *Panax quiquefolium* tablets, *Ophiocordyceps sinensis* 5X, but these preparations have single effect and are expensive, moreover, the anti-aging effect is not significant.

Based upon this, with the guidance of the theory of the traditional Chinese medicine, and combined with decades of clinical research and medication experience, the inventor repeatedly optimizes and adjusts the recipe to obtain the composition of the present invention finally; the composition has the efficacy of dredging the channel, regulating Qi functions of visceral organs, expelling vivotoxins, supplementing human nutrition, improving internal circulation, enhancing body functions and delaying aging.

SUMMARY

A technical problem to be solved by the present invention is to provide a composition for improving internal circulation, enhancing body functions, and delaying aging.

Another technical problem to be solved by the present invention is to provide an application of the composition in improving internal circulation, enhancing body functions and delaying aging.

The specific technical solutions of the present invention are as follows:

The present invention provides a composition for improving internal circulation, enhancing body functions and delaying aging, including the following materials in parts by weight: 5-100 parts of *Rosa roxburghii*, 5-100 parts of *Phyllanthus emblica*, 5-100 parts of honey, 1-30 parts of walnuts and 1-30 parts of *Citrus limon*.

Preferably, the composition includes the following materials in parts by weight: 10-80 parts of *Rosa roxburghii*, 10-80 parts of *Phyllanthus emblica*, 10-80 parts of honey, 2-20 parts of walnuts and 2-20 parts of *Citrus limon*.

Preferably, the composition includes the following materials in parts by weight: 15-50 parts of *Rosa roxburghii*, 15-50 parts of *Phyllanthus emblica*, 10-50 parts of honey, 5-20 parts of walnuts and 5-20 parts of *Citrus limon*.

The present invention provides a preparation method of the composition, where the composition is prepared as follows: *Rosa roxburghii*, *Phyllanthus emblica*, walnut and *Citrus limon* are taken, ground or cut into slices, then extracted by alcohol and percolated, an extracting solution or percolate is collected and added honey for mixing well to be prepared into oral preparations; or the medicinal materials or food materials are taken, fermented or soaked into oral preparations.

Preferably, the oral preparations of the present invention are medicinal liquors, oral liquids, tinctures, etc.

The present invention provides an application of the composition, namely, an application in the preparation of drugs, health-care food and food for improving internal circulation, enhancing body functions and delaying aging.

In this recipe, the efficacy of ingredients is as follows:

*Rosa roxburghii*: it is recorded in *A Supplement to the Compendium of Materia Medica* that *Rosa roxburghii* has the efficacy of promoting digestion and tonifying spleen, astringing to arrest diarrhea and relieving summer-heat, and modern studies indicate that *Rosa roxburghii* has the efficacy of regulating body immunity, delaying aging, detoxifying, resisting atherosclerosis and tumor, etc. in addition to application in the treatment of retention of food, abdominal distension, dysentery, enteritis, hypertension, vascular rupture hemorrhage, vitamin C deficiency and other diseases.

*Phyllanthus emblica*: tastes sweet, sour, astringent and cool, classified into meridian tropism of lung and stomach, and has the efficacy of removing pathogenic heat from blood, promoting digestion and invigorating stomach, promoting the secretion of saliva and relieving a cough, mainly used for treating blood-heat/blood stasis, dyspepsia, abdominal distension, cough, sore throat and thirst.

Honey: tastes sweet, mild, classified into meridian tropism of lung, spleen and large intestine, and has the efficacy of strengthening the middle warmer, moistening dryness, relieving pain, detoxifying, used for treating stomach/abdomen pain, lung dryness and dry cough, intestinal dryness with constipation, and detoxifying monkshood agents.

Walnut: tastes sweet and warm, classified into meridian tropism of kidney, lung and large intestine, and has the efficacy of tonifying kidney, warming lung and lubricating intestine, and can be used in the treatment of kidney-yang insufficiency, soreness and weakness of waist and knees, impotence and spermatorrhea, deficiency-cold, cough and asthma, intestinal dryness with constipation.

*Citrus limon*: has the efficacy of promoting the secretion of saliva, quenching thirst, clearing away summer heat, dredging stagnation, invigorating stomach, relieving pain, treating stasis, stomachache and loss of appetite.

The recipe is obtained by clinical practices and optimization for many years under the guidance of basic theory of traditional Chinese medicine. *Rosa roxburghii*, *Phyllanthus emblica* and *Citrus limon* in the recipe have the efficacy of invigorating spleen to promote digestion and the secretion of saliva, and may regulate body Qi functions of visceral organs and spleen governing functions, thus promoting the absorption of nutrient substances in food and the acceleration of vivotoxins excretion, meanwhile, the above drugs contain rich mineral substances, vitamins, SOD and amino acids which are nutrients required by human body, capable of supplementing human nutrition, enhancing body functions, resisting cell aging and delaying aging while improving internal circulation; in the recipe, walnut is classified into meridian tropism of kidney, lung and large intestine, and has the efficacy of tonifying kidney, warming lung and lubricating intestine, capable of regulating and restoring main visceral functions of human body, improving internal circulation, rebuilding and enhancing immunity; in the recipe, honey has the efficacy of strengthening the middle warmer, moistening dryness, relieving pain and detoxifying, moreover rich in multiple fructoses and vitamins required by our body, which is not only beneficial to discharging faeces remaining in body and clearing away vivotoxins, but also has the effect of supplementing human nutrients, achieving compatibility of drugs efficacy and modifying the taste, thus further enhancing the efficacy of the recipe, namely, regulating the Qi functions of visceral organs, expelling vivotoxins, supplementing human nutrition, improving internal circulation and enhancing body functions. To sum up, the recipe is reasonable and its major ingredients are coordinated and supplemented with each other to achieve medical compatibility, meanwhile, the recipe has stronger effect of improving internal circulation, enhancing body functions and delaying aging.

The beneficial effects of the present invention are:

1) The composition of the present invention is made by conventional medicinal materials and food materials via based upon a scientific recipe under the guidance of basic theory of traditional Chinese medicine; the composition has significant effect in improving internal circulation, enhancing body functions and delaying aging, and may be widely applied in all kinds of people, thus satisfying people's demand for improving internal circulation, enhancing body functions and delaying aging.

2) Raw materials of the composition provided by the present invention are all from pure-natural Chinese herbal medicine or conventional food, moreover, the composition has wide sources, no toxic and side effects, cheap, green and healthy, suitable for large-scale popularization and application.

DETAILED DESCRIPTION

The present invention will be described more specifically with reference to embodiments. It should be appreciated that implementation of the present invention is not limited to the embodiments below, and various changes and/or modifications made to the present invention in any form will fall within the scope of the present invention.

In the present invention, all parts and percentages are a unit of weight unless otherwise specified. Methods in the following embodiments are conventional methods of the field unless otherwise specified; in the present invention, the *Rosa roxburghii*, *Phyllanthus emblica*, walnut and *Citrus limon* may be fresh or dried products.

Embodiment 1: 100 g *Rosa roxburghii*, 100 g *Phyllanthus emblica*, 60 g honey, 30 g walnuts and 15 g *Citrus limon* were taken and added 5 times of 50° white spirit according to gross weight of the recipe, soaked for 30 d and filtered, a soup was collected.

Embodiment 2: 5 g *Rosa roxburghii*, 10 g *Phyllanthus emblica*, 3 g walnuts and 1 g *Citrus limon* were taken and crushed into coarse powder, soaked by 50° white spirit, and percolated for extraction at 1 ml/min, then, 2 times of percolate was collected according to the weight of the recipe, 5 g honey was added to the percolate for mixing well.

Embodiment 3: 40 g *Rosa roxburghii*, 40 g *Phyllanthus emblica*, 30 g honey, 15 g walnut and 10 g *Citrus limon* were taken and added 4 times of 50° white spirit according to gross weight of the recipe, soaked for 30 d and filtered, a soup was collected.

Embodiment 4: 30 g *Rosa roxburghii*, 25 g *Phyllanthus emblica*, 10 g walnuts and 5 g *Citrus limon* were taken and crushed into coarse powder, soaked by 50° white spirit, and percolated for extraction at 3 ml/min, then, 3 times of percolate was collected according to the weight of the recipe, 20 g honey was added to the percolate for mixing well.

Embodiment 5: 15 g *Rosa roxburghii*, 10 g *Phyllanthus emblica*, 10 g walnuts and 5 g *Citrus limon* were taken and added 6 times of water according to gross weight of the medicinal materials, soaked for half an hour and extracted for twice 2 h each time, and filtered, then an extracting solution is blended and added 10 g honey for mixing well.

Embodiment 6: 15 g *Rosa roxburghii*, 20 g *Phyllanthus emblica*, 15 g honey, 1 g walnut and 3 g *Citrus limon* were taken and added 4 times of water according to gross weight of the recipe, put into a cool place for fermentation for 30 d, then filtered, a fermentation broth was collected.

Embodiment 7: 10 kg *Rosa roxburghii*, 6 kg *Phyllanthus emblica*, 6 kg walnuts, 9 kg honey and 3 kg *Citrus limon* were taken and added 5 times of 50° white spirit according to gross weight of the recipe, soaked for 30 d and filtered, a soup was collected and subpackaged into 100 ml/bottle.

Embodiment 8: 100 kg *Rosa roxburghii*, 90 kg *Phyllanthus emblica*, 30 kg walnuts and 25 kg *Citrus limon* were taken and added 4 times of water according to gross weight of the medicinal materials, soaked for half an hour and extracted for twice 2 h each time, and filtered, then an extracting solution is blended and added 3 kg honey for mixing well, and subpackaged into 100 ml/bottle.

Embodiment 9: 5 kg *Rosa roxburghii*, 3 kg *Phyllanthus emblica*, 6 kg walnuts and 6 kg *Citrus limon* were taken and soaked by 50° white spirit for staying overnight, and percolated for extraction at 20 ml/min, then, 3 times of percolate was collected according to the weight of the recipe, 4 kg honey was added to the percolate for mixing well, and subpackaged into 100 ml/bottle.

Embodiment 10: 6 kg *Rosa roxburghii*, 6 kg *Phyllanthus emblica*, 10 kg honey, 2 kg walnuts and 2 kg *Citrus limon* were taken and added 4 times of water according to gross weight of the recipe, put into a cool place for fermentation for 30 d, then filtered, a fermentation broth was collected, and subpackaged into 100 ml/bottle.

Embodiment 11: Clinical effect of the composition of the present invention

The composition of the present invention may improve internal circulation and enhance body functions better, thus delaying aging by dredging the channel, regulating Qi functions of visceral organs, expelling vivotoxins and supplementing human nutrition. Clinical research data and data of the composition are as follows: 237 cases were selected from March 2011 to November 2016, and the inclusion criteria: patients suffered lassitude, amnesia, intolerance of cold and cold limbs, poor appetite and insomnia, waist-leg weakness, hair loss and loose tooth, short breath and tiredness and other common senile symptoms. Therapies: the composition in Embodiment 10 of the present invention was taken for three times per day, 100 ml each time, a course of treatment lasted 3 weeks and three courses were observed totally, and other anti-aging drugs were withdrawn during administration. Therapeutic outcome:

(1) Overall clinical efficacy: 134 cases were remarkably effective, accounting for 56.54%; 62 cases were effective, accounting for 26.16%; 41 cases were ineffective, accounting for 17.30%. The total effective rate was 196 cases, accounting for 82.70%.

(2) Improvement effect on clinical common senile symptoms was shown in table 1 below:

TABLE 1

Improvement effect of the composition on common clinical senile symptoms

| Groups | Number of cases | Remarkably effective | | Effective | | Ineffective | |
|---|---|---|---|---|---|---|---|
| | | Number of cases | Percent age (%) | Number of cases | Percent age (%) | Number of cases | Percent age (%) |
| Lassitude | 215 | 123 | 57 | 60 | 28 | 32 | 15 |
| Waist-leg weakness | 217 | 114 | 53 | 51 | 24 | 52 | 24 |
| Amnesia | 187 | 92 | 49 | 38 | 20 | 57 | 30 |
| Poor appetite and insomnia | 174 | 97 | 56 | 55 | 32 | 22 | 13 |
| Short breath and tiredness | 165 | 81 | 49 | 38 | 23 | 46 | 28 |
| Hair loss and loose tooth | 154 | 76 | 49 | 45 | 29 | 33 | 21 |
| Intolerance of cold and cold limbs | 144 | 69 | 48 | 39 | 27 | 36 | 25 |

It can be seen the above table that the composition may improve common various clinical symptoms caused by human aging to different extents, and has remarkable efficacy in enhancement of patients' functions, delay of aging and other aspects.

To sum up, by clinical observation of aging syndrome and lab data analysis, the results show that the composition of the present invention has remarkable efficacy in channel dredging, regulation of Qi functions of visceral organs, expelling of vivotoxins, supplementary of human nutrition, improvement of internal circulation, enhancement of body functions and delay of aging, moreover, the composition has no adverse reaction and side effects.

Embodiment 12: Anti-aging test

The anti-aging effect of the composition of the present invention was researched by a life test for *Drosophila melanogaster* (provided by Animal Genetics Teaching and Research Office of College of Life Science of Southwest University), a blank control group (distilled water), a control group of incomplete recipe (containing *Rosa roxburghii* only, containing *Phyllanthus emblica* and *Phyllanthus emblica*, containing *Rosa roxburghii*, *Phyllanthus emblica* and walnut) and a control group (Embodiment 2 (the solution obtained after removing ethanol), Embodiment 6 and Embodiment 8) were set, average life (an arithmetic average of the total life of *Drosophila melanogaster* in each group) and maximum life (an arithmetic average of the life of the last surviving 10 *Drosophila melanogaster* in each group) served as evaluation indexes to evaluate the aging resistance of the composition of the present invention.

Preparation of a basic media: 100 g corn flour, 135 g sucrose, 10 g yeast powder, 1.5 g benzoic acid (dissolved by 4 ml 95% ethanol), 15 g agar and 740 ml distilled water (containing test samples of treatment groups) were prepared into a blank medium without samples and a medium containing 1% of test samples (in the incomplete recipe group, samples in each group were added via a form of converted decoction liquor prepared by corresponding medicinal materials and water; in the treatment group, samples in embodiments were added after converted, and the addition: per 100 g medium contained 1 g raw medicinal materials after converted) for further use.

Treatment and Culture of *Drosophila melanogaster*

700 pieces of feathered and non-mated *Drosophila melanogaster* were collected within 8 h, narcotized by ether and divided into 7 groups, namely, blank control group, *Rosa roxburghii* group, *Rosa roxburghii*+*Phyllanthus emblica* group, *Rosa roxburghii*+*Phyllanthus emblica*+walnut group, group of Embodiment 2, group of Embodiment 6 and group of Embodiment 8. There were 100 pieces in each group for half male and half female, respectively put into corresponding culture flasks for culture, and the culture flasks were sealed by plugs prepared by coating gauze on sterilized degreasing cotton, put into a thermostatic incubator $(25\pm1)°$ C., and the media were replaced every 5 d.

Observation Index 7 groups were observed at 9: 30 every morning and number of the dead flies was recorded excepting for the dead caused by excessive anesthesia or sticking by media and other human factors. An arithmetic average of the life of the last 10 surviving *Drosophila melanogaster* served as the maximum life of the group; an arithmetic average of the total life of *Drosophila melanogaster* in each group served as the average life of the group.

Experimental Results

Influences of samples in each group on the average life and maximum life of *Drosophila melanogaster* were shown in table 2.

TABLE 2

Influences of samples in each group on the average life and maximum life of *Drosophila melanogaster*

| Groups | Number of *Drosophila melanogaster* | Average life (d) | Maximum life (d) |
|---|---|---|---|
| Blank control | 68 | 59 ± 20.52 | 85 ± 11.31 |
| *Rosa roxburghii* | 77 | 65 ± 14.35 | 91 ± 9.49 |
| *Rosa roxburghii* + *Phyllanthus emblica* | 71 | 66 ± 8.51 | 93 ± 12.77 |
| *Rosa roxburghii* + *Phyllanthus emblica* + walnut | 68 | 64 ± 15.27 | 94 ± 8.92 |
| Embodiment 2 | 74 | 75 ± 11.34* | 102 ± 7.96* |
| Embodiment 6 | 79 | 73 ± 9.68* | 105 ± 5.38* |
| Embodiment 8 | 83 | 77 ± 12.21* | 100 ± 6.82* |

*Compared with blank control group, it had statistic difference (p < 0.05)

The above researches show that compared with the blank control group and the group of incomplete recipe, the composition of the present invention may remarkably extend the life of *Drosophila melanogaster*, thereby the composition of the present invention has remarkable effect in aging delaying.

Embodiment 13: Antioxidation Experiment

Oxidation effect of the composition of the present invention was researched by two in-vitro antioxidant models, namely, 1,1-diphenyl picryl phenylhydrazine (DPPH) free radicals and hydroxyl radicals. A blank control group (distilled water), a control group of incomplete recipe (containing *Rosa roxburghii* only, containing *Rosa roxburghii* and *Phyllanthus emblica*, containing *Rosa roxburghii*, *Phyllanthus emblica* and walnut) and treatment groups (Embodiment 5, Embodiment 7 (the solution obtained after removing ethanol), Embodiment 10) were set; in the incomplete recipe group, samples in each group were obtained by decocting corresponding medicinal materials and water for concentration (1 ml concentrated liquor was equivalent to 1 g raw medicinal materials); and in treatment groups, samples in embodiments were obtained by concentrating the samples thereof (1 ml concentrated liquor was equivalent to 1 g raw medicinal materials), and the experimental method was as follows:

Measurement of Scavenging Activity of DPPH Free Radicals:

Samples were taken and diluted by distilled water for 10 times to obtain the samples to be tested. 0.2 mL samples to be tested were exactly taken to test tubes, 2.0 mL (0.4 mmol/L) DPPH and 70% ethanol solution were added for oscillation evenly, and the 2.0 mL (0.4 mmol/L) DPPH and 70% ethanol solution were mixed as a blank control group, reaction was performed in a dark place at room temperature, then absorbance values were measured at 517 nm wavelength, and 70% ethanol served as a reference for zero setting. Calculation method of the clearance rate of DPPH free radicals:

$$Y = \frac{A_0 - A}{A_0} \times 100\%$$

in the formula: $A_0$ is an absorbance value of the control sample at 517 nm; A is an absorbance value of the sample.

Measurement of Scavenging Activity of Hydroxyl Radicals:

Samples were taken and diluted by distilled water for 10 times to obtain the samples to be tested. 0.25 mL FeSO4 (2 mmol/L), 0.5 mL salicylic acid (6 mmol/L) and 1 mL samples to be tested were successively added to a reaction system for mixing well, then 0.25 mL $H_2O_2$ (mass fraction: 0.01%) was added. Reaction was performed for 30 min at 37° C. for cooling, and then absorbance was measured at 510 nm. Calculation method of the clearance rate (%) of hydroxyl radicals:

$$\Box\Box Z = \frac{Z_0 - (Z_i - Z_{i0})}{Z_0} \times 100\%$$

in the formula: $Z_0$ is an absorbance value of the blank control group; $Z_i$ is an absorbance value of the group with samples; $Z_{i0}$ is an absorbance value of the group without $H_2O_2$, a color developing agent.

Experimental results are shown in Table 3.

TABLE 3

Results of the in-vitro antioxidant experiment

| Groups | DPPH clearance ratio (%) | Clearance ratio of hydroxyl radicals (%) |
|---|---|---|
| Blank control | 0 | 0 |
| *Rosa roxburghii* | 56.52 ± 4.63 | 64.71 ± 5.32 |
| *Rosa roxburghii* + *Phyllanthus emblica* | 63.11 ± 7.02 | 68.93 ± 6.71 |
| *Rosa roxburghii* + *Phyllanthus emblica* + walnut | 73.24 ± 4.93 | 79.24 ± 8.45 |
| Embodiment 5 | 79.74 ± 11.28 | 83.76 ± 12.87 |
| Embodiment 7 | 93.28 ± 10.84 | 97.31 ± 12.49 |
| Embodiment 10 | 85.02 ± 11.32 | 89.09 ± 12.91 |

*Each experiment was repeated for three times.

Results of the antioxidation experiment show that compared with the blank control group and the group of incomplete recipe, the composition of the present invention may remarkably clear away DPPH free radicals and hydroxyl radicals, thereby the composition of the present invention has remarkable effect in antioxidation.

What is claimed is:

1. A therapeutic composition for treating amnesia, insomnia or hair loss in a human in need thereof consisting essentially of 15-50 parts of *Rosa roxburghii,* 15-50 parts of *Phyllanthus emblica,* 15-50 parts of honey, 5-20 parts of walnuts and 5-20 parts of *Citrus limon.*

2. The therapeutic composition of claim 1, which is made by grinding or cutting into slices *Rosa roxburghii, Phyllanthus emblica,* walnut and *Citrus limon* and then extracting with alcohol and percolating the resulting mixture, then adding honey to the resulting mixture to produce the composition of claim 1.

3. A method of treating amnesia, insomnia or hair loss in a human in need thereof consisting essentially of administering to the human in need thereof 15-50 parts of *Rosa roxburghii,* 15-50 parts of *Phyllanthus emblica,* 15-50 parts of honey, 5-20 parts of walnuts and 5-20 parts of *Citrus limon.*

* * * * *